(12) United States Patent
Inada et al.

(10) Patent No.: US 6,645,445 B1
(45) Date of Patent: Nov. 11, 2003

(54) PROCESS FOR REMOVING TITANIUM OXIDE OR RED OXIDE FROM ETHYLENE GLYCOL

(75) Inventors: Shuji Inada, Suita (JP); Kikuchi Sato, Fukuyama (JP)

(73) Assignee: Aies Co., Ltd., Tokyo (JP)

( * ) Notice: Subject to any disclaimer, the term of this patent is extended or adjusted under 35 U.S.C. 154(b) by 239 days.

(21) Appl. No.: 09/831,010

(22) PCT Filed: Sep. 5, 2000

(86) PCT No.: PCT/JP00/06010
§ 371 (c)(1),
(2), (4) Date: May 3, 2001

(87) PCT Pub. No.: WO01/19775
PCT Pub. Date: Mar. 22, 2001

(30) Foreign Application Priority Data

| Sep. 9, 1999 | (JP) | ............................................. 11-255118 |
| Apr. 26, 2000 | (JP) | ....................................... 2000-125371 |
| Apr. 26, 2000 | (JP) | ....................................... 2000-125372 |

(51) Int. Cl.$^7$ ............................................... C01G 23/02
(52) U.S. Cl. ......................... 423/84; 423/610; 423/633; 423/140; 23/313 R
(58) Field of Search .............................. 423/84, 70, 71, 423/80, 86, 139, 140, 150.1, 633; 23/313 R

(56) References Cited

U.S. PATENT DOCUMENTS 5,158,651 A * 10/1992 Doerr ........................... 203/33

FOREIGN PATENT DOCUMENTS

| JP | 45-41215 | 12/1970 |
| JP | 50-71639 | 6/1975 |

* cited by examiner

Primary Examiner—Stanley S. Silverman
Assistant Examiner—Edward M. Johnson
(74) Attorney, Agent, or Firm—Anderson Kill & Olick, P.C.; Eugene Lieberstein; Michael N. Meller

(57) ABSTRACT

A process for efficiently removing titanium oxide or red oxide from an ethylene glycol solvolysis product of a polyester containing titanium oxide or red oxide. The process comprises the steps of:

(1) mixing at least one calcium compound selected from the group consisting of calcium oxide, calcium carbonate and calcium hydroxide with a polyester decomposition product containing titanium oxide which is an ethylene glycol solvolysis product of a polyester containing titanium oxide to agglomerate titanium oxide contained in the polyester decomposition product, or mixing titanium oxide with a polyester decomposition product containing red oxide which is an ethylene glycol solvolysis product of a polyester containing red oxide to agglomerate red oxide contained in the polyester decomposition product; and (2) subjecting the agglomerates to solid-liquid separation to remove titanium oxide or red oxide from the polyester decomposition product.

11 Claims, No Drawings

PROCESS FOR REMOVING TITANIUM OXIDE OR RED OXIDE FROM ETHYLENE GLYCOL

FIELD OF THE INVENTION

The present invention relates to a process for efficiently removing titanium oxide or red oxide from an ethylene glycol solvolysis product of a polyester containing titanium oxide or red oxide by agglomerating titanium oxide or red oxide.

PRIOR ART

Currently, the main application field of bis-β-hydroxyethyl terephthalate is terephthalate-based polyesters and one of the features of the terephthalate-based polyesters is that they have performance well suited to a wide range of fields of molded products such as fibers, films and resins. Especially in the field of fibers out of the wide range of fields, titanium oxide is generally contained in a polymer mainly to draw polish. Mainly in the field of molded products such as bottles, red oxide is experimentally or will be commercially made existent in a polymer. Meanwhile, another feature of the polyesters is that it is relatively easy to restore the polyesters to their raw material stages by depolymerization.

Polyesters, particularly terephthalate-based polyesters typified by polyethylene terephthalate are widely used for various purposes as described above. To produce the polyesters, a process in which an intermediate containing bis-β-hydroxyethyl terephthalate is obtained by direct esterification between terephthalic acid and ethylene glycol or an ester exchange reaction between a lower alkyl ester of terephthalic acid, especially dimethyl terephthalate and ethylene glycol and then polycondensed at a high temperature under high vacuum is now mainly used practically. Further, the terephthalate-based polyesters can be restored to their raw material stages by depolymerization and polymerized again to obtain polyesters. Therefore, it can be said that they are excellent materials from the viewpoint of resource saving.

However, when recovered polyesters are polyesters containing titanium oxide or polyesters containing red oxide, the content of the titanium oxide or red oxide and the types and contents of other additives change by each recovered polyester and become a barrier to the separation of a substance of interest after a depolymerization reaction in many cases. Therefore, actual operation is frequently impeded.

SUMMARY OF THE INVENTION

It is an object of the present invention to provide a process for removing titanium oxide from an ethylene glycol solvolysis product of a polyester containing titanium oxide with high operation ease and high efficiency.

It is another object of the present invention to provide a process for obtaining a polyester decomposition product containing substantially no titanium oxide by efficiently removing titanium oxide from an ethylene glycol solvolysis product of a polyester containing titanium oxide.

It is still another object of the present invention to provide a process for efficiently removing titanium oxide from an ethylene glycol solvolysis product of a recovered polyester to enable and facilitate recycling of the recovered polyester containing titanium oxide.

It is a further object of the present invention to provide a process for removing red oxide from an ethylene glycol solvolysis product of a polyester containing red oxide with high operation ease and high efficiency.

It is a still further object of the present invention to provide a process for obtaining a polyester decomposition product containing substantially no red oxide by efficiently removing red oxide from an ethylene glycol solvolysis product of a polyester containing red oxide.

It is a still further object of the present invention to provide a process for efficiently removing red oxide from an ethylene glycol solvolysis product of a recovered polyester to enable and facilitate recycling of the recovered polyester containing red oxide.

It is a still further object of the present invention to provide a process for removing red oxide from even a polyester containing red oxide and further carbon black with high operation ease and high efficiency.

Other objects and advantages of the present invention will become apparent from the following description.

According to the present invention, firstly, the above objects and advantages of the present invention are attained by a process for removing titanium oxide from a polyester decomposition product (to be referred to as "first process of the present invention" hereinafter) which comprises the steps of:

(1) mixing at least one compound (may be referred to as "specific compound" hereinafter) selected from the group consisting of calcium oxide, calcium carbonate, calcium hydroxide and red oxide with a polyester decomposition product containing titanium oxide which is an ethylene glycol solvolysis product of a polyester containing titanium oxide to agglomerate titanium oxide contained in the polyester decomposition product; and (2) subjecting the agglomerated titanium oxide to solid-liquid separation to remove it.

According to the present invention, secondly, the above objects and advantages of the present invention are attained by a process for removing red oxide from a polyester decomposition product (to be referred to as "second process of the present invention" hereinafter) which comprises the steps of:

(1) mixing titanium oxide with a polyester decomposition product containing red oxide which is an ethylene glycol solvolysis product of a polyester containing red oxide to agglomerate red oxide contained in the polyester decomposition product; and (2) subjecting the agglomerates to solid-liquid separation to remove them.

A description is first given of the first process of the present invention.

In the present invention, the polyester to be decomposed by adding ethylene glycol contains titanium oxide. The content of titanium oxide is 10 wt % or less, preferably 2 wt % or less, more preferably 0.5 wt % or less based on the polyester.

The type of polyester is not limited but preferably an aromatic polyester comprising an aromatic dicarboxylic acid such as terephthalic acid or 2,6-naphthalenedicarboxylic acid as the main dicarboxylic acid component and ethylene glycol as the main glycol component. Out of these, a terephthalate-based polyester comprising ethylene terephthalate as the main constitute component is particularly preferred.

In the present invention, the terephthalate-based polyester is what comprises polyethylene terephthalate as the main constituent component and is also including what copolymerizes at least one other constituent component in a small proportion. The proportion of the copolymerizable component is preferably 40 mol % or less, more preferably 30 mol % or less, much more preferably 20 mol % or less based on the total of all the acid components and all the glycol components. Examples of the copolymerizable component include dicarboxylic acids such as aromatic dicarboxylic acids exemplified by isophthalic acid, diphenyldicarboxylic acid, diphenylsulfonedicarboxylic acid, diphenyl ether dicarboxylic acid, naphthalenedicarboxylic acid, diphenoxyethane dicarboxylic acid and sodium sulfoisophthalic acid, aliphatic dicarboxylic acids exemplified by sebacic acid and adipic acid, and alicyclic dicarboxylic acids exemplified by hexahydroterephthalic acid; and diols such as trimethylene glycol, tetramethylene glycol, hexamethylene glycol, cyclohexane dimethanol, bis-β-hydroxyethyl bisphenol A, bis-β-hydroxyethoxydiphenyl sulfone, bis-β-hydroxyethoxydiphenyl ether, diethylene glycol, polyethylene glycol and the like. A hydroxycarboxylic acid such as p-hydroxyethoxyphenyl carboxylic acid may be used as the copolymerizable component. Further, a polyfunctional compound having a functionality of 3 or more and/or a monofunctional compound may also be used as the copolymerizable component in limits that the polyester keeps linear. Examples of the polyfunctional compound having a functionality of 3 or more include trimesic acid, glycerin, pentaerythritol and the like, and examples of the monofunctional compound include diphenylmonocarboxylic acid, diphenyl ether monocarboxylic acid, phenoxypolyethylene glycol and the like. These copolymerizable components may be used as a functional derivative such as an ester. They may be used alone or in combination of two or more.

The terephthalate-based polyester may be used in various forms such as pellet, flake, filament and block.

In the process of the present invention, an ethylene glycol solvolysis product of a polyester containing titanium oxide is first prepared. Solvolysis with ethylene glycol may be carried out under reaction conditions known per se. Ethylene glycol is preferably used in an amount of 300 to 500 parts by weight based on 100 parts by weight of the polyester containing titanium oxide. The reaction temperature is preferably 200 to 220° C. and the reaction may be carried out for 2.5 to 5.0 hours. It is recommended to add an appropriate reaction catalyst for the reaction. Examples of the reaction catalyst include known ester exchange reaction catalysts such as methylates of sodium and magnesium, aliphatic acid salts of zinc cadmium, manganese, cobalt, calcium, barium and the like typified by zinc borate and zinc acetate, carbonates thereof, metal sodium, metal magnesium and oxides thereof, and the like. They may be used alone or in combination of two or more. The amount of the reaction catalyst added is generally 0.05 to 3.0 wt % based on the terephthalate-based polyester as a raw material.

In the first process of the present invention, the above specific compound is mixed with the above ethylene glycol solvolysis product to agglomerate titanium oxide. Specific methods for carrying out this include (i) one in which before the solvolysis with ethylene glycol of a polyester containing titanium oxide is carried out, the polyester and the specific compound are combined, subjected to an ethylene glycol solvolytic reaction and mixed, (ii) one in which the polyester is subjected to solvolysis with ethylene glycol, and the specific compound is added to a reaction system during a reaction before solvolysis with ethylene glycol is completed and mixed, or (iii) one in which the specific compound is added to a decomposition product obtained after the completion of the solvolysis with ethylene glycol of the polyester and mixed. These methods may be used in combination of two or more. These methods can be carried out at an increased pressure, normal pressure or reduced pressure if they do not prevent the ethylene glycol solvolytic reaction.

In the above methods (i) and (ii), the ethylene glycol solvolytic reaction is carried out in the presence of the specific compound. Therefore, the specific compound is uniformly mixed into the obtained polyester decomposition product and titanium oxide can be agglomerated by cooling the obtained polyester decomposition product in this case.

In the above method (iii), the ethylene glycol solvolytic reaction is carried out in the absence of the specific compound and the specific compound is added after the completion of solvolysis with ethylene glycol. In this case, after the specific compound is added, titanium oxide can be agglomerated effectively by heating preferably at a temperature of 150° C. or more for 10 minutes or more.

For the above solvolysis with ethylene glycol, the following two methods may be carried on. (1) an excessive amount of ethylene glycol is added to the polyester itself to decompose the polyester or (2) the polyester is pre-decomposed by heating together with bis-(β-hydroxyethyl) terephthalate and/or a polyester low condensate and an excessive amount of ethylene glycol is added to the obtained pre-decomposition product to decompose the product.

In the above methods (i), (ii) and (iii), the specific compound may be added one time or a plurality of times at different times. Out of these methods, the above method (i) is particularly preferred.

The specific compound is calcium oxide, calcium carbonate, calcium hydroxide or red oxide. These specific compounds may be used alone or in combination of two or more.

Red oxide which is generally used as a colorant may be used as the above red oxide without hindrance.

The specific compound is preferably added as a slurry in ethylene glycol.

The specific compound is preferably used in an amount of 0.1 to 5.0 parts by weight, more preferably 0.5 to 2.5 parts by weight, particularly preferably 0.8 to 1.5 parts by weight based on 1 part by weight of titanium oxide contained in the polyester to be decomposed.

Although the reason why the addition of the specific compound is greatly effective in the agglomeration of titanium oxide is unknown yet, it is considered that the specific compound causes some chemical reaction with titanium oxide.

The above specific compound used in the present invention is relatively hardly soluble in ethylene glycol. Calcium chloride and calcium acetate which are soluble in ethylene glycol cannot be used.

According to the results of studies conducted by the present inventor, when calcium sulfate which is widely used is used as the specific compound, it promotes a side reaction that the amount of diethylene glycol increases and at the same time causes an increase in the amount of load in the deanionization step which will be described hereinafter.

In the second step of the process of the present invention, the polyester decomposition product containing agglomerated titanium oxide obtained in the first step is subjected to solid-liquid separation to remove the agglomerated titanium oxide.

The solid-liquid separation may be carried out by a method known per se, for example, filtration or centrifugation.

According to the present invention, a polyester decomposition product containing substantially no titanium oxide, for example, a polyester decomposition product consisting of bis-β-hydroxyethyl terephthalate is obtained.

A description is subsequently given of the second process of the present invention.

It should be understood that a description which titanium oxide to be removed in the above description of the first process of the present invention is replaced by red oxide, is applied to the second process of the present invention except the following description.

A process in which a polyester containing titanium oxide is used, that is, a red oxide-containing polyester and a titanium oxide-containing polyester are both subjected to solvolysis with ethylene glycol and mixed together in substantial embodiment the first step is also included in the present invention. When an ethylene glycol solvolytic reaction is carried out in the absence of titanium oxide and titanium oxide is added after the completion of solvolysis with ethylene glycol (corresponding to embodiment of the above (iii)), red oxide can be effectively agglomerated by heating preferably at a temperature of 190 to 280° C. for 0.5 to 5 hours after titanium oxide is added.

Titanium oxide may be in any crystal form such as anatase or rutile type. These titanium oxides may be used alone or in combination. The titanium oxide is preferably added as a slurry in ethylene glycol.

Titanium oxide is preferably used in an amount of 0.1 to 10 parts by weight, more preferably 0.2 to 8.0 parts by weight, particularly preferably 0.3 to 5.0 parts by weight based on 1 part by weight of red oxide contained in the polyester to be decomposed.

Although the reason why the addition of titanium oxide is greatly effective in the agglomeration of red oxide is unknown yet, it is considered that titanium oxide causes some chemical or physical interaction with red oxide.

Titanium oxide used in the present invention is hardly soluble in ethylene glycol. Titanium butoxide which is soluble in ethylene glycol cannot be used.

When the polyester contains carbon black in addition to red oxide, the present invention can be carried out almost similarly. In this case, carbon black and red oxide form agglomerates with titanium oxide.

The second step of the process of the present invention is carried out by removing agglomerates by subjecting the polyester decomposition product containing agglomerated titanium oxide obtained from the first step to solid-liquid separation.

The solid-liquid separation may be carried out by a method known per se, for example, filtration or centrifugation.

According to the present invention, after the solid-liquid separation, a polyester decomposition product containing substantially no red oxide or no carbon black according to circumstances, for example, a polyester decomposition product consisting of bis-β-hydroxyethyl terephthalate is obtained.

A description common to the first process of the present invention and the second process of the present invention will be given hereinafter.

The polyester decomposition product obtained by the present invention is then preferably deanionized and decationized. That is, the polyester decomposition product is contacted to a cation exchanger and an anion exchanger preferably in a solids content of 5 to 80 wt % to reduce its ion content to 50 ppm or less.

The cation exchanger and the anion exchanger may be, for example, in a particulate, chain, fibrous or amorphous form. For example, a particulate ion exchanger is charged into a column and a solution composition is caused to pass through the column to contact the ion exchanger.

The cation exchanger is preferably a cation exchange resin and the anion exchanger is preferably an anion exchange resin.

The cation exchange resin is preferably what has —SO₃H, —COOH, —N(CH₂COOH)₂ or the like as a cation exchange functional group. Examples of the cation exchange resin include commercially available SK series, PK series and WK series of Dia Ion (of Mitsubishi Chemical Corporation) and IR series and IRC series of Amberlite (of Rohm and Harse Japan Co., Ltd.). Since the ion exchange functional groups of these products are generally stabilized as a salt such as sodium salt, they are generally converted into free acid groups as described above when in use.

The anion exchange resin is what has an anion exchange functional group such as

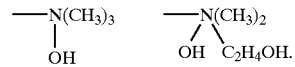

Examples of the anion exchange resin include commercially available SA series, PA series and WA series of Dia Ion (Mitsubishi Chemical Corporation) and IRA series and IRAC-900 series of Amberlite (of Rohm and Harse Japan Co., Ltd.). Since the ion exchange functional groups of these products are generally stabilized as what have a halogen anion and not a hydroxide ion (OH⁻), they are converted into what have a hydroxyl group anion as described above when in use.

The anion exchange resin is available in cracked and non-cracked gel types. The non-cracked gel type is preferred because the amount of bis-β-hydroxyethyl terephthalate absorbed is small.

Further, a so-called microporous ion exchange resin having higher physical durability and higher exchange absorption rate than a gel type ion exchange resin may also be used.

Either one or both of the cation exchanger and the anion exchanger may be used. For example, when a solution composition containing both cations and anions as impurities may contain one of them in a larger amount than the other one and the amount of the other one is negligibly small, only one ion exchanger for removing the first ions may be used.

Generally speaking, both a cation exchanger and an anion exchanger are preferably used. In this case, the solution composition may be contacted to the cation exchanger and anion exchanger simultaneously or sequentially. For example, the solution composition may be contacted to a mixture of a cation exchange resin and an anion exchange resin simultaneously or contacted to a column filled with a cation exchange resin and a column filled with an anion exchange resin sequentially. Preferably, the solution composition is contacted to a cation exchanger and then an anion exchanger sequentially.

The contact between the cation exchanger/anion exchanger and the solution composition must be carried out at a temperature below the highest use temperature of the ion exchange resins, preferably 20 to 120° C., more preferably 30 to 70° C. without the precipitation of the crystals of bis-β-hydroxyethyl terephthalate from a solvent.

The contact may be carried out at a normal pressure, reduced pressure or increased pressure. Needless to say, the contact is carried out under such conditions as concentration, temperature and pressure at which the solution composition can keep its solution state.

In the present invention, after the solution composition is contacted to ion exchangers, bis-β-hydroxyethyl terephthalate with a small ion content which contains cations as an impurity in an amount of 50 ppm or less based on bis-β-hydroxyethyl terephthalate is obtained.

According to the results of studies conducted by the present inventor, a polyester obtained from bis-β-hydroxyethyl terephthalate obtained by using the process of the present invention as one of its production raw materials can be used as molded products such as fibers, films and bottles without a problem.

Further, when depolymerized product composed of substantially bis-β-hydroxyethyl terephthalate is to be obtained by depolymerizing these polyester molded products, the depolymerized product obtained by carrying out a depolymerization step using an excessive amount of ethylene glycol as described above can be generally obtained as a liquid composition comprising bis-β-hydroxyethyl terephthalate and ethylene glycol as the main solvent. High-quality bis-β-hydroxyethyl terephthalate can be obtained from this composition directly or by adjusting the concentration of the composition to an appropriate level or by removing a catalyst as required. In this case, before, during or after this step, the decolorization step is carried out at least one time as required to obtain high-quality bis-β-hydroxyethyl terephthalate easily.

Bis-β-hydroxyethyl terephthalate obtained by using the process of the present invention can be used as at least one of raw materials for the re-production of a high-quality polyester in a solution state directly, in the form of a solution whose concentration has been adjusted to a appropriate level, or after it is subjected to a recyrstallization step or distillation step. In this case, even when a polyester molded product to be depolymerized is mixed with other material or mixed with foreign matter such as dust as in the case of a commercial product, the present invention can be carried out without hindrance by using a foreign matter removing step such as separation or filtration as required. Giving specific examples, when a polyester is in the form of a fibrous commercial product, it is mixed with a different type of fibers or contains various substances such as a dye and pigment, when a polyester is in the form of a film, it is mixed with a different type of film material or contains various additives such as a lubricant used in the polyester, when a polyester is in the form of other molded product such as a bottle, it is crushed and mixed with a different type of material such as polyethylene used in a cover portion or bottom portion, or mixed with a different type of material such as paper or plastic used in a label. Although these situations are rather general, according to the results of studies conducted by the present inventor, a predetermined object can be attained completely by using conventional known techniques such as liquid-liquid separation and solid-liquid separation and the process of the present invention and various techniques described above as required.

The following examples are given to further illustrate the present invention. It is needless to say that the present invention is not limited to these examples only.

EXAMPLES

Example 1

(1) 12 kg of used polyester bedding cotton (hollow type, 6 denier×51 mm, titanium oxide content of 0.397 wt %, intrinsic viscosity of 0.630) and 6 kg of bis-β-hydroxyethyl terephthalate were charged into a 150-liter autoclave with a jacket (with an anchor type stirrer) and the polyester was pre-decomposed by gradually elevating the temperature at a stirrer revolution of 5 rpm to obtain an oligomer in a molten state heated at 225° C. in about 30 minutes.

Thereafter, 70 kg of ethylene glycol, 60 g of sodium methylate and 60 g of calcium hydroxide were added to the obtained oligomer to carry out the depolymerization of the oligomer at normal pressure and a temperature below the boiling point of ethylene glycol for about 60 minutes to obtain a polyethylene terephthaiate depolymerization product.

This depoymerization product was cooled to 85° C., extruded by applying a gauge pressure of 19,600 Pa (0.2 kg/cm$^2$) to the autoclave with nitrogen gas and at the same time filtered with a 10 μm polypropylene fiber cartridge type filter installed in the extraction port of the autoclave while the temperature was maintained. The obtained filtered solution of the depolymerization product was fully transparent visually and the precipitation of titanium oxide was not observed at all.

(2) Thereafter, 80 kg of ethylene glycol heated at normal temperature was added to this depolymerization solution to obtain a solution containing ethylene glycol as the main solvent and bis-β-hydroxyethyl terephthalate as the main solute. This solution was totally decolorized with activated carbon at a temperature of 55° C., decationized with a cation exchange resin (Amberlite IR120-B of Organo Co., Ltd.) and deanionized with an anion exchange resin (Amberlite IRA-400 of Organo Co., Ltd.). The decationized and deanionized solution was charged into a 500-liter autoclave equipped with a stirrer and vacuum generator, ethylene glycol was distilled off at 135° C. and 10,670 Pa (80 mmHg) until the content of ethylene glycol in the solution became 20%, the resulting solution was concentrated with a vacuum thin film evaporator having a heat transfer area of 0.5 m$^2$ at 150° C. and 200 Pa (1.5 mmHg) until the total content of substances having a lower boiling point than the boiling point of bis-β-hydroxyethyl terephthalate became 5.0 wt % to obtain a composition comprising crude bis-β-hydroxyethyl terephthalate, and this composition containing crude bis-β-hydroxyethyl terephthalate was subjected to molecular distillation with a molecular distiller having a heat transfer area of 0.5 m$^2$ for 75 minutes at 200° C. and 24 Pa (0.18 mmHg) to obtain purified bis-β-hydroxyethyl terephthalate. The quality analytical values of the obtained purified bis-β-hydroxyethyl terephthalate are shown in Table 1. Thereafter, 500 g of normal-temperature powders of the obtained purified bis-β-hydroxyethyl terephthalate were injected into a 1,000 cc glass polymerizer with a stirrer, the inside of the polymerizer was fully substituted with nitrogen gas, bis-β-hydroxyethyl terephthalate was molten by heating at 130° C. under a nitrogen gas atmosphere, 2.7 g of a solution containing 0.2 part by weight of germanium dioxide prepared by completely dissolving hexagonal germanium dioxide in boiled ethylene glycol was added as a polymerization catalyst under a nitrogen gas atmosphere, the temperature was elevated to the boiling point (197° C.) of ethylene glycol over 20 minutes under agitation, and heating and stirring were further carried out at normal pressure and 197° C. for 45 minutes to obtain an oligomer for polyethylene terephthalate. Subsequently, this oligomer was polycondensed at 280° C. and 90 Pa (0.7 mmHg) for 2 hours to obtain polyethylene terephthalate. The quality analytical values of the obtained polyethylene terephthalate are shown in Table 2. The purified bis-β-hydroxyethyl terephthalate and polyethylene terephthalate were of extremely excellent quality for practical use.

TABLE 1

| | | |
|---|---|---|
| 1 | optical density | 0.059 |
| 2 | acid value (KOH mg/g) | 0.4 |
| 3 | saponification value (KOH mg/g) | 439 |
| 4 | melting point (° C.) | 112 |
| 5 | Whiteness | L = 98.7, a = −0.7, b = 1.2 |
| 6 | total cation content (ppm) | 0.76 |
| 7 | total anion content (ppm) | 0 |
| 8 | bis-β-hydroxyethyl terephthalate (wt %) | 97.93 |
| 9 | mono-β-hydroxyethyl terephthalate (wt %) | 1.33 |
| 10 | oligomer (wt %) | 0.74 |

The term "optical density" in Table 1 is an index for evaluating the quality of bis-β-hydroxyethyl terephthalate and proportional to the content of a colored product. It is obtained by measuring the absorbance of a 10% methanol solution at a wavelength of 380 nm and a cell length of 10 mm. The whiteness was measured with a color differential meter and represented by "L" (brightness), "a" (redness) and "b" (yellowness) values of a Hunter method.

TABLE 2

| | | |
|---|---|---|
| 1 | intrinsic viscosity ([η]) | 0.695 |
| 2 | diethylene glycol (wt %) | 1.11 |
| 3 | carboxyl terminal group (μeq/g) | 9.9 |
| 4 | whiteness | L = 83.0, a = −2.2, b = −4.5 |

The intrinsic viscosity in Table 2 was measured in orthochlorophenol at 30° C. The whiteness was measured with a color difference meter and represented by "L" (brightness), "a" (redness) and "b" (yellowness) values of the Hunter method.

Example 2

The depolymerization product of polyethylene terephthalate was obtained under the same conditions as in Example 1 except that calcium carbonate fine powders were used in place of calcium hydroxide of Example 1. The obtained filtered solution of the depolymerization product was fully transparent visually and the precipitation of titanium oxide was not observed at all.

Purified bis-β-hydroxyethyl terephthalate and polyethylene terephthalate were formed from this filtered solution as a raw material under the same conditions as in Example 1 and were of extremely excellent quality for practical use.

Comparative Example 1

10 kg of used polyethylene terephthalate short fibers containing 0.4% of titanium oxide as a delustering agent and 72 kg of ethylene glycol were charged into a 240-liter autoclave with a stirrer and 0.07 kg of sodium methylate as a known ester exchange catalyst was added to depolymerize a PET bottle and polyethylene terephthalate short fibers by heating and stirring at 200° C. and normal pressure for 3 hours. Agglomerates of titanium oxide were existent in the solution obtained by depolymerization and the depolymerization solution was cloudy. This depolymerization solution was totally decolorized with activated carbon at a temperature of 55° C., decationized with a cation exchange resin (Amberlite IR120-B of Organo Co., Ltd.) and deanionized with an anion exchange resin (Amberlite of Organo Co., Ltd.). The agglomerates of titanium oxide blocked up columns filled with the ion exchange resins, thereby making impossible continuous stable operation.

Example 3

2,840 g of ethylene glycol, 2 g of sodium methylate as a catalyst and 8 g of titanium oxide were added to 400 g of crushed pieces of a colored sheet formed by adding red oxide of a pigment grade and carbon black to a polyethylene terephthalate resin in a total amount of 2 wt % to carry out depolymerization in a 4-liter autoclave at 220° C. and 0.15 MPa for 3 hours. The obtained depolymerization solution was cooled and maintained at 55±3° C. for 3 hours to crystallize an oligomer and filtered with a 0.8 to 1 μm membrane filter while the temperature was maintained at that level to remove coarse agglomerated particles of red oxide, carbon black and titanium oxide and crystallized oligomer. Thereafter, the solution was decolorized and deionized, cooled to 0 to 5° C. with −5° C. brine to crystallize and separate crude bis-β-hydroxyethyl terephthalate, low-boiling substances were distilled off from the crystals at 9.31 KPa (70 Torr) and 133° C., and molecular distillation was carried out at 13 Pa (0.1 Torr) and 187° C. to obtain bis-β-hydroxyethyl terephthalate having a purity of 99.0% and an "L" value of 97.0, an "a" value of −0.60 and a "b" value of 0.90 (Hunter values).

What is claimed is:

1. A process for removing titanium oxide from a polyester decomposition product comprising the steps of:
   (1) mixing at least one compound selected from the group consisting of calcium oxide, calcium carbonate, calcium hydroxide and red oxide with a polyester decomposition product containing titanium oxide which is an ethylene glycol solvolysis product of a polyester containing titanium oxide to agglomerate titanium oxide contained in the polyester decomposition product; and
   (2) subjecting the agglomerated titanium oxide to solid-liquid separation to remove it.

2. The process of claim 1, wherein the polyester containing titanium oxide is polyethylene terephthalate containing titanium oxide.

3. The process of claim 1, wherein the above compound is used in an amount of 0.1 to 5.0 parts by weight based on 1 part by weight of titanium oxide contained in the polyester.

4. The process of claim 1, wherein the above compound is added to the polyester decomposition product after solvolysis with ethylene glycol and heated at a temperature of 150° C. or more for 10 minutes or more to agglomerate titanium oxide.

5. The process of claim 1, wherein the amount of free ethylene glycol contained in the polyester decomposition product is at least 5 wt % based on the decomposition product.

6. A process for removing red oxide from a polyester decomposition product comprising the steps of:
   (1) mixing titanium oxide with a polyester decomposition product containing red oxide which is an ethylene glycol solvolysis product of a polyester containing red oxide to agglomerate red oxide contained in the polyester decomposition product; and
   (2) subjecting the agglomerates to solid-liquid separation to remove them.

7. The process of claim 6, wherein the polyester containing red oxide is polyethylene terephthalate containing red oxide.

8. The process of claim 6, wherein titanium oxide is used in an amount of 0.1 to 10 parts by weight based on 1 part by weight of red oxide contained in the polyester.

9. The process of claim 6, wherein titanium oxide is mixed with the polyester decomposition product at a temperature of 190 to 280° C. for 0.5 to 5 hours.

10. The process of claim 6, wherein the polyester decomposition product contains free ethylene glycol in an amount of at least 5 wt % based on the decomposition product.

11. The process of claim 6, wherein the polyester containing red oxide further contains carbon black.

* * * * *